(12) United States Patent
Argento et al.

(10) Patent No.: US 11,266,496 B2
(45) Date of Patent: Mar. 8, 2022

(54) ADJUSTABLE OPTICAL POWER INTRAOCULAR LENSES

(71) Applicant: Shifamed Holdings, LLC, Campbell, CA (US)

(72) Inventors: Claudio Argento, Felton, CA (US); Tom Saul, Moss Beach, CA (US); Colin Mixter, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/619,602

(22) PCT Filed: Jun. 7, 2018

(86) PCT No.: PCT/US2018/036548
§ 371 (c)(1),
(2) Date: Dec. 5, 2019

(87) PCT Pub. No.: WO2018/227014
PCT Pub. Date: Dec. 13, 2018

(65) Prior Publication Data
US 2020/0146813 A1    May 14, 2020

Related U.S. Application Data

(60) Provisional application No. 62/516,541, filed on Jun. 7, 2017.

(51) Int. Cl.
*A61F 2/16* (2006.01)
*A61F 2/48* (2006.01)

(52) U.S. Cl.
CPC .......... *A61F 2/1635* (2013.01); *A61F 2/1648* (2013.01); *A61F 2/484* (2021.08);
(Continued)

(58) Field of Classification Search
None
See application file for complete search history.

(56) References Cited

U.S. PATENT DOCUMENTS

| 4,440,918 A | 4/1984 | Rice et al. |
| 4,663,409 A | 5/1987 | Friends et al. |

(Continued)

FOREIGN PATENT DOCUMENTS

| AU | 2006200142 A1 | 7/2006 |
| AU | 2015361227 | 4/2017 |

(Continued)

OTHER PUBLICATIONS

Klank, et al. "CO2-laser micromachining and back-end processing for rapid production of PMMA-based microfluidic systems," Lab Chip, 2002, 2, 242-246.

(Continued)

*Primary Examiner* — Leslie Lopez
(74) *Attorney, Agent, or Firm* — Perkins Coie LLP

(57) ABSTRACT

The present technology is directed to an adjustable power intraocular lens comprising a container, an optical fluid in the container, and a transport substance in solution with the optical fluid. The container has an optical component and a peripheral component extending around at least a portion of the optical component. The optical component has an anterior optical element, a posterior optical element, and a fluid chamber having a chamber volume between the anterior optical element and the posterior optical element. The transport substance is configured to pass through the container. The adjustable power intraocular lens further comprises volume control elements in the container. The volume control elements are configured to be activated by a non-invasive energy and upon activation release the transport substance into the optical fluid to decrease the chamber (Continued)

volume and/or absorb the transport substance from the optical fluid to increase the chamber volume.

15 Claims, 6 Drawing Sheets

(52) U.S. Cl.
CPC .............. *A61F 2210/0061* (2013.01); *A61F 2210/0066* (2013.01); *A61F 2250/0013* (2013.01)

(56) References Cited

U.S. PATENT DOCUMENTS

| | | | |
|---|---|---|---|
| 4,709,996 A * | 12/1987 | Michelson | A61F 2/1616 351/159.04 |
| 4,731,078 A | 3/1988 | Stoy et al. | |
| 4,731,080 A | 3/1988 | Galin | |
| 4,842,601 A | 6/1989 | Smith et al. | |
| 4,892,543 A | 1/1990 | Turley | |
| 4,932,966 A | 6/1990 | McMaster et al. | |
| 4,932,971 A | 6/1990 | Kelman | |
| 5,074,942 A | 12/1991 | Orlosky et al. | |
| 5,211,662 A | 5/1993 | Barrett et al. | |
| 5,217,491 A | 6/1993 | Vanderbilt | |
| 5,366,502 A | 11/1994 | Patel | |
| 5,405,386 A | 4/1995 | Rheinish et al. | |
| 5,423,929 A | 6/1995 | Grisoni et al. | |
| 5,489,302 A | 2/1996 | Skottun | |
| 5,556,929 A | 9/1996 | Yokoyama et al. | |
| 5,612,391 A | 3/1997 | Chabrecek et al. | |
| 5,620,720 A | 4/1997 | Glick et al. | |
| 5,807,944 A | 9/1998 | Hirt et al. | |
| 5,891,931 A | 4/1999 | Leboeuf et al. | |
| 5,914,355 A | 6/1999 | Kuenzler | |
| 5,944,753 A | 8/1999 | Galin et al. | |
| 5,945,465 A | 8/1999 | Ozark et al. | |
| 5,945,498 A | 8/1999 | Lohmann et al. | |
| 6,140,438 A | 10/2000 | Kawaguchi et al. | |
| 6,346,594 B1 | 2/2002 | Watanabe et al. | |
| 6,447,920 B1 | 9/2002 | Chabrecek et al. | |
| 6,465,056 B1 | 10/2002 | Chabrecek et al. | |
| 6,521,352 B1 | 2/2003 | Lohmann et al. | |
| 6,537,316 B1 | 3/2003 | Chambers | |
| 6,558,420 B2 | 5/2003 | Green et al. | |
| 6,582,754 B1 | 6/2003 | Pasic et al. | |
| 6,586,038 B1 | 7/2003 | Chabrecek et al. | |
| 6,630,243 B2 | 10/2003 | Ozark et al. | |
| 6,660,035 B1 | 12/2003 | Yaross et al. | |
| 6,685,741 B2 | 2/2004 | Landreville et al. | |
| 6,695,881 B2 | 2/2004 | Peng et al. | |
| 6,713,583 B2 | 3/2004 | Liao et al. | |
| 6,730,123 B1 | 5/2004 | Klopotek et al. | |
| 6,734,321 B2 | 5/2004 | Chabrecek et al. | |
| 6,747,090 B2 | 6/2004 | Haitjema et al. | |
| 6,761,737 B2 | 7/2004 | Ting et al. | |
| 6,764,511 B2 | 7/2004 | Ting et al. | |
| 6,767,363 B1 | 7/2004 | Green et al. | |
| 6,767,979 B1 | 7/2004 | Muir et al. | |
| 6,786,934 B2 | 9/2004 | Ting et al. | |
| 6,797,004 B1 | 9/2004 | Brady et al. | |
| 6,818,017 B1 | 11/2004 | Shu et al. | |
| 6,818,158 B2 | 11/2004 | Pham et al. | |
| 6,835,410 B2 | 12/2004 | Chabrecek et al. | |
| 6,846,326 B2 | 1/2005 | Nguyen et al. | |
| 6,858,040 B2 | 2/2005 | Ting et al. | |
| 6,884,261 B2 | 4/2005 | Zadno-Azizi et al. | |
| 6,893,595 B1 | 5/2005 | Muir et al. | |
| 6,893,685 B2 | 5/2005 | Pasic et al. | |
| 6,899,732 B2 | 5/2005 | Zadno-Azizi et al. | |
| 6,935,743 B2 | 8/2005 | Shadduck | |
| 6,969,403 B2 | 11/2005 | Yang et al. | |
| 7,041,134 B2 | 5/2006 | Ting et al. | |
| 7,087,080 B2 | 8/2006 | Ting et al. | |
| 7,097,660 B2 | 8/2006 | Portney | |
| 7,118,596 B2 | 10/2006 | Ting et al. | |
| 7,198,640 B2 | 4/2007 | Nguyen | |
| 7,217,778 B2 | 5/2007 | Flipsen et al. | |
| 7,226,478 B2 | 6/2007 | Ting et al. | |
| 7,300,464 B2 | 11/2007 | Tran | |
| 7,416,562 B2 | 8/2008 | Gross et al. | |
| 7,438,723 B2 | 10/2008 | Esch | |
| 7,452,378 B2 | 11/2008 | Ting et al. | |
| 7,468,397 B2 | 12/2008 | Schorzman et al. | |
| 7,479,530 B2 | 1/2009 | Chan et al. | |
| 7,557,231 B2 | 7/2009 | Schorzman et al. | |
| 7,588,334 B2 | 9/2009 | Matsushita et al. | |
| 7,591,849 B2 | 9/2009 | Richardson et al. | |
| 7,601,766 B2 | 10/2009 | Schorzman et al. | |
| 7,637,947 B2 | 12/2009 | Scholl et al. | |
| 7,714,090 B2 | 5/2010 | Iwamoto et al. | |
| 7,744,603 B2 | 6/2010 | Zadno-Azizi et al. | |
| 7,744,646 B2 | 6/2010 | Zadno-Azizi et al. | |
| 7,781,558 B2 | 8/2010 | Schorzman et al. | |
| 7,806,929 B2 | 10/2010 | Brown et al. | |
| 7,806,930 B2 | 10/2010 | Brown et al. | |
| 7,842,087 B2 | 11/2010 | Ben | |
| 7,883,540 B2 | 2/2011 | Niwa et al. | |
| 7,906,563 B2 | 3/2011 | Huang et al. | |
| 7,942,929 B2 | 5/2011 | Linhardt et al. | |
| 8,003,710 B2 | 8/2011 | Medina et al. | |
| 8,025,823 B2 | 9/2011 | Figueroa et al. | |
| 8,034,107 B2 | 10/2011 | Stenger et al. | |
| 8,048,155 B2 | 11/2011 | Shadduck et al. | |
| 8,071,703 B2 | 12/2011 | Zhou et al. | |
| 8,105,623 B2 | 1/2012 | Schorzman et al. | |
| 8,158,712 B2 | 4/2012 | Your | |
| 8,187,325 B2 | 5/2012 | Zadno-Azizi et al. | |
| 8,211,955 B2 | 7/2012 | Chang et al. | |
| 8,222,360 B2 | 7/2012 | Liao | |
| 8,251,509 B2 | 8/2012 | Zickler et al. | |
| 8,283,429 B2 | 10/2012 | Zhou et al. | |
| 8,328,869 B2 | 12/2012 | Burns et al. | |
| 8,357,771 B2 | 1/2013 | Medina et al. | |
| 8,377,123 B2 | 2/2013 | Zadno et al. | |
| 8,414,646 B2 | 4/2013 | Gifford et al. | |
| 8,420,711 B2 | 4/2013 | Awasthi et al. | |
| 8,425,595 B2 | 4/2013 | Evans et al. | |
| 8,425,599 B2 | 4/2013 | Shadduck et al. | |
| 8,425,926 B2 | 4/2013 | Qiu et al. | |
| 8,430,928 B2 | 4/2013 | Liao | |
| 8,454,688 B2 | 6/2013 | Evans et al. | |
| 8,486,142 B2 | 7/2013 | Bumbalough et al. | |
| 8,500,806 B1 | 8/2013 | Phillips et al. | |
| 8,585,758 B2 | 11/2013 | Woods | |
| 8,603,166 B2 | 12/2013 | Park | |
| 8,609,745 B2 | 12/2013 | Medina et al. | |
| 8,663,510 B2 | 3/2014 | Graney et al. | |
| 8,680,172 B2 | 3/2014 | Liao | |
| 8,728,158 B2 | 5/2014 | Whitsett | |
| 8,759,414 B2 | 6/2014 | Winter et al. | |
| 8,784,485 B2 | 7/2014 | Evans et al. | |
| 8,827,447 B2 | 9/2014 | Awasthi et al. | |
| 8,834,566 B1 | 9/2014 | Jones | |
| 8,835,525 B2 | 9/2014 | Chang et al. | |
| 8,851,670 B2 | 10/2014 | Zickler et al. | |
| 8,863,749 B2 | 10/2014 | Gooding et al. | |
| 8,877,227 B2 | 11/2014 | Ravi | |
| 8,899,745 B2 | 12/2014 | Domschke | |
| 8,900,298 B2 | 12/2014 | Chazan et al. | |
| 8,956,409 B2 | 2/2015 | Ben | |
| 8,968,399 B2 | 3/2015 | Ghabra | |
| 8,992,609 B2 | 3/2015 | Shadduck | |
| 8,993,651 B2 | 3/2015 | Chang et al. | |
| 9,005,492 B2 | 4/2015 | Chang et al. | |
| 9,005,700 B2 | 4/2015 | Qiu et al. | |
| 9,006,359 B2 | 4/2015 | Schultz et al. | |
| 9,011,532 B2 | 4/2015 | Catlin et al. | |
| 9,023,915 B2 | 5/2015 | Hu et al. | |
| 9,034,035 B2 | 5/2015 | Assia et al. | |
| 9,039,174 B2 | 5/2015 | Awasthi et al. | |
| 9,044,302 B2 | 6/2015 | Gooding et al. | |
| 9,052,439 B2 | 6/2015 | Samuel et al. | |

(56) References Cited

U.S. PATENT DOCUMENTS

| | | |
|---|---|---|
| 9,052,440 B2 | 6/2015 | Chang et al. |
| 9,095,424 B2 | 8/2015 | Atkinson et al. |
| 9,097,840 B2 | 8/2015 | Chang et al. |
| 9,125,736 B2 | 9/2015 | Atkinson et al. |
| 9,186,244 B2 | 11/2015 | Rao et al. |
| 9,198,572 B2 | 12/2015 | Zickler et al. |
| 9,198,752 B2 | 12/2015 | Woods |
| 9,254,189 B2 | 2/2016 | Azar et al. |
| 9,265,604 B2 | 2/2016 | Woods |
| 9,280,000 B2 | 3/2016 | Simonov et al. |
| 9,289,287 B2 | 3/2016 | Atkinson et al. |
| 9,326,848 B2 | 5/2016 | Woods |
| 9,364,316 B1 | 6/2016 | Kahook et al. |
| 9,387,069 B2 | 7/2016 | Atkinson et al. |
| 9,398,949 B2 | 7/2016 | Werblin |
| 9,421,088 B1 | 8/2016 | Schieber et al. |
| 9,427,312 B2 | 8/2016 | Tai et al. |
| 9,456,895 B2 | 10/2016 | Shadduck et al. |
| 9,486,311 B2 | 11/2016 | Vaughan et al. |
| 9,498,326 B2 | 11/2016 | Tsai et al. |
| 9,603,703 B2 | 3/2017 | Bumbalough |
| 9,622,855 B2 | 4/2017 | Portney et al. |
| 9,636,213 B2 | 5/2017 | Brady |
| 9,655,775 B2 | 5/2017 | Boukhny et al. |
| 9,681,946 B2 | 6/2017 | Kahook et al. |
| 9,693,858 B2 | 7/2017 | Hildebrand et al. |
| 9,744,027 B2 | 8/2017 | Jansen |
| 9,795,473 B2 | 10/2017 | Smiley et al. |
| 9,814,568 B2 | 11/2017 | Ben Nun |
| 9,907,881 B2 | 3/2018 | Terrisse |
| 10,195,018 B2 | 2/2019 | Salahieh et al. |
| 10,350,057 B2 | 7/2019 | Argento et al. |
| 10,526,353 B2 | 1/2020 | Silvestrini |
| 10,548,718 B2 | 2/2020 | Salahieh et al. |
| 10,709,549 B2 | 7/2020 | Argento et al. |
| 10,736,734 B2 | 8/2020 | Salahieh et al. |
| 11,065,109 B2 | 7/2021 | Argento et al. |
| 2001/0037001 A1 | 11/2001 | Muller et al. |
| 2001/0056165 A1 | 12/2001 | Mentak et al. |
| 2002/0072795 A1 | 6/2002 | Green et al. |
| 2002/0086160 A1 | 7/2002 | Qiu et al. |
| 2002/0102415 A1 | 8/2002 | Valint, Jr. et al. |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0138141 A1 | 9/2002 | Zadno-Azizi et al. |
| 2002/0173847 A1 | 11/2002 | Pham et al. |
| 2002/0197414 A1 | 12/2002 | Chabrecek et al. |
| 2003/0008063 A1 | 1/2003 | Chabrecek et al. |
| 2003/0074060 A1 | 4/2003 | Zadno-Azizi et al. |
| 2003/0074061 A1 | 4/2003 | Pham et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0100666 A1 | 5/2003 | DeGroot et al. |
| 2003/0158560 A1 | 8/2003 | Portney |
| 2003/0162929 A1 | 8/2003 | Verbruggen et al. |
| 2003/0224185 A1 | 12/2003 | Valint, Jr. et al. |
| 2004/0082993 A1 | 4/2004 | Woods |
| 2004/0111152 A1 | 6/2004 | Kelman et al. |
| 2004/0166232 A1 | 8/2004 | Kunzler et al. |
| 2004/0169816 A1 | 9/2004 | Esch |
| 2004/0184158 A1 | 9/2004 | Shadduck |
| 2004/0230300 A1 | 11/2004 | Bandhauer et al. |
| 2005/0013842 A1 | 1/2005 | Qiu et al. |
| 2005/0049700 A1 | 3/2005 | Zadno-Azizi et al. |
| 2005/0055092 A1 | 3/2005 | Nguyen et al. |
| 2005/0149183 A1 | 7/2005 | Shadduck et al. |
| 2005/0153055 A1 | 7/2005 | Ammon et al. |
| 2005/0165410 A1 | 7/2005 | Zadno-Azizi et al. |
| 2005/0228120 A1 | 10/2005 | Hughes et al. |
| 2005/0228401 A1 | 10/2005 | Zadno-Azizi et al. |
| 2006/0069432 A1 | 3/2006 | Tran |
| 2006/0100701 A1 | 5/2006 | Esch et al. |
| 2006/0100703 A1 | 5/2006 | Evans et al. |
| 2006/0116765 A1 | 6/2006 | Blake et al. |
| 2006/0178741 A1 | 8/2006 | Zadno-Azizi et al. |
| 2006/0241752 A1 | 10/2006 | Israel |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0050025 A1 | 3/2007 | Nguyen et al. |
| 2007/0078515 A1 | 4/2007 | Brady |
| 2007/0088433 A1* | 4/2007 | Esch ................ A61F 2/1648 623/6.13 |
| 2007/0092830 A1 | 4/2007 | Lai et al. |
| 2007/0106377 A1 | 5/2007 | Smith et al. |
| 2007/0108643 A1 | 5/2007 | Zadno-Azizi et al. |
| 2007/0122540 A1 | 5/2007 | Salamone et al. |
| 2007/0201138 A1 | 8/2007 | Lo et al. |
| 2007/0203317 A1 | 8/2007 | Verbruggen et al. |
| 2007/0213817 A1 | 9/2007 | Esch et al. |
| 2007/0232755 A1 | 10/2007 | Matsushita et al. |
| 2007/0269488 A1 | 11/2007 | Ravi et al. |
| 2008/0001318 A1 | 1/2008 | Schorzman et al. |
| 2008/0003259 A1 | 1/2008 | Salamone et al. |
| 2008/0003261 A1 | 1/2008 | Schorzman et al. |
| 2008/0015689 A1 | 1/2008 | Esch et al. |
| 2008/0027461 A1 | 1/2008 | Vaquero et al. |
| 2008/0046074 A1 | 2/2008 | Smith et al. |
| 2008/0076897 A1 | 3/2008 | Kunzler et al. |
| 2008/0139769 A1 | 6/2008 | Iwamoto et al. |
| 2008/0143958 A1 | 6/2008 | Medina et al. |
| 2008/0181931 A1 | 7/2008 | Qiu et al. |
| 2008/0234457 A1 | 9/2008 | Zhou et al. |
| 2008/0300680 A1 | 12/2008 | Joshua et al. |
| 2008/0314767 A1 | 12/2008 | Lai et al. |
| 2009/0043384 A1 | 2/2009 | Niwa et al. |
| 2009/0076603 A1 | 3/2009 | Avery et al. |
| 2009/0118739 A1 | 5/2009 | Kappelhof et al. |
| 2009/0143499 A1 | 6/2009 | Chang et al. |
| 2009/0168012 A1 | 7/2009 | Linhardt et al. |
| 2009/0170976 A1 | 7/2009 | Huang et al. |
| 2009/0171459 A1 | 7/2009 | Linhardt et al. |
| 2009/0204210 A1 | 8/2009 | Pynson |
| 2009/0232871 A1 | 9/2009 | Hitz et al. |
| 2009/0247661 A1 | 10/2009 | Muller-Lierheim et al. |
| 2009/0292355 A1 | 11/2009 | Boyd et al. |
| 2010/0016964 A1 | 1/2010 | Werblin |
| 2010/0119744 A1 | 5/2010 | Yokoyama et al. |
| 2010/0120938 A1 | 5/2010 | Phelan et al. |
| 2010/0120939 A1 | 5/2010 | Phelan et al. |
| 2010/0121444 A1 | 5/2010 | Ben et al. |
| 2010/0160482 A1 | 6/2010 | Nachbaur et al. |
| 2010/0179653 A1 | 7/2010 | Argento et al. |
| 2010/0211170 A1 | 8/2010 | Liao et al. |
| 2010/0228346 A1 | 9/2010 | Esch et al. |
| 2010/0239633 A1 | 9/2010 | Strome et al. |
| 2010/0324674 A1 | 12/2010 | Brown et al. |
| 2011/0009519 A1 | 1/2011 | Awasthi et al. |
| 2011/0046332 A1 | 2/2011 | Breiner et al. |
| 2011/0112636 A1 | 5/2011 | Ben Nun |
| 2011/0118379 A1 | 5/2011 | Tighe et al. |
| 2011/0118834 A1 | 5/2011 | Lo et al. |
| 2011/0133350 A1 | 6/2011 | Qiu et al. |
| 2011/0140292 A1 | 6/2011 | Chang et al. |
| 2011/0144228 A1 | 6/2011 | Ravi et al. |
| 2011/0269869 A1 | 11/2011 | Medina et al. |
| 2011/0282442 A1 | 11/2011 | Scholl et al. |
| 2011/0295368 A1 | 12/2011 | Betser |
| 2012/0010321 A1 | 1/2012 | Chang et al. |
| 2012/0023869 A1 | 2/2012 | Samuel et al. |
| 2012/0033183 A1 | 2/2012 | Dai et al. |
| 2012/0041097 A1 | 2/2012 | Zhou et al. |
| 2012/0046743 A1 | 2/2012 | Pinchuk et al. |
| 2012/0063000 A1 | 3/2012 | Batchko et al. |
| 2012/0078363 A1 | 3/2012 | Lu |
| 2012/0078364 A1 | 3/2012 | Stenger |
| 2012/0088843 A1 | 4/2012 | Chang et al. |

(56) References Cited

U.S. PATENT DOCUMENTS

| | | |
|---|---|---|
| 2012/0088844 A1 | 4/2012 | Kuyu et al. |
| 2012/0088861 A1 | 4/2012 | Huang et al. |
| 2012/0115979 A1 | 5/2012 | Chang et al. |
| 2012/0147323 A1 | 6/2012 | Domschke et al. |
| 2012/0238857 A1 | 9/2012 | Wong et al. |
| 2012/0245684 A1 | 9/2012 | Liao et al. |
| 2012/0314183 A1 | 12/2012 | Nakamura et al. |
| 2012/0330415 A1 | 12/2012 | Callahan et al. |
| 2013/0013060 A1 | 1/2013 | Zadno-Azizi et al. |
| 2013/0053954 A1 | 2/2013 | Rao et al. |
| 2013/0095235 A1 | 4/2013 | Bothe et al. |
| 2013/0106007 A1 | 5/2013 | Medina et al. |
| 2013/0110234 A1 | 5/2013 | DeVita et al. |
| 2013/0116781 A1 | 5/2013 | Ben Nun et al. |
| 2013/0150961 A1 | 6/2013 | Evans et al. |
| 2013/0176628 A1 | 7/2013 | Batchko et al. |
| 2013/0197125 A1 | 8/2013 | Awasthi et al. |
| 2013/0224309 A1 | 8/2013 | Qiu et al. |
| 2013/0228943 A1 | 9/2013 | Qiu et al. |
| 2013/0245756 A1 | 9/2013 | Liao et al. |
| 2013/0289294 A1 | 10/2013 | Awasthi et al. |
| 2013/0304203 A1 | 11/2013 | Beer |
| 2013/0317607 A1 | 11/2013 | DeBoer et al. |
| 2014/0055750 A1 | 2/2014 | Dai et al. |
| 2014/0171539 A1 | 6/2014 | Chang et al. |
| 2014/0171542 A1 | 6/2014 | Chang |
| 2014/0178595 A1 | 6/2014 | Bothe et al. |
| 2014/0180403 A1 | 6/2014 | Silvestrini et al. |
| 2014/0180406 A1 | 6/2014 | Simpson |
| 2014/0180407 A1 | 6/2014 | Sohn et al. |
| 2014/0228949 A1 | 8/2014 | Argento et al. |
| 2014/0277439 A1 | 9/2014 | Hu et al. |
| 2014/0309735 A1 | 10/2014 | Sohn et al. |
| 2014/0316521 A1 | 10/2014 | McLeod et al. |
| 2014/0350124 A1 | 11/2014 | Chang et al. |
| 2014/0379079 A1 | 12/2014 | Ben Nun |
| 2015/0088149 A1 | 3/2015 | Auld |
| 2015/0092155 A1 | 4/2015 | Chang et al. |
| 2015/0105760 A1 | 4/2015 | Silvestrini et al. |
| 2015/0152228 A1 | 6/2015 | Chang et al. |
| 2015/0164321 A1 | 6/2015 | Weibel et al. |
| 2015/0173892 A1 | 6/2015 | Borja et al. |
| 2015/0177417 A1 | 6/2015 | Goshima et al. |
| 2015/0351901 A1 | 12/2015 | Chicevic et al. |
| 2016/0000558 A1 | 1/2016 | Honigsbaum et al. |
| 2016/0008126 A1 | 1/2016 | Vaughan et al. |
| 2016/0030161 A1 | 2/2016 | Rao et al. |
| 2016/0058553 A1 | 3/2016 | Vaughan et al. |
| 2016/0074154 A1 | 3/2016 | Woods |
| 2016/0100938 A1 | 4/2016 | Weeber et al. |
| 2016/0128826 A1 | 5/2016 | Rao et al. |
| 2016/0151150 A1 | 6/2016 | Sato |
| 2016/0184091 A1 | 6/2016 | Burns et al. |
| 2016/0184092 A1 | 6/2016 | Flaherty et al. |
| 2016/0250020 A1 | 9/2016 | Schieber et al. |
| 2016/0256265 A1 | 9/2016 | Borja et al. |
| 2016/0262875 A1 | 9/2016 | Smiley et al. |
| 2016/0278914 A1 | 9/2016 | Sato et al. |
| 2016/0296320 A1 | 10/2016 | Humayun et al. |
| 2016/0296662 A1 | 10/2016 | Dudic et al. |
| 2016/0317286 A1 | 11/2016 | Rao et al. |
| 2016/0317287 A1 | 11/2016 | Rao et al. |
| 2016/0331587 A1 | 11/2016 | Ueno et al. |
| 2016/0361157 A1 | 12/2016 | Honigsbaum |
| 2017/0000602 A1 | 1/2017 | Sohn et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0119521 A1 | 5/2017 | Kahook et al. |
| 2017/0258581 A1 | 9/2017 | Borja et al. |
| 2017/0348094 A1 | 12/2017 | Sohn et al. |
| 2018/0110613 A1 | 4/2018 | Wortz et al. |
| 2018/0161152 A1 | 6/2018 | Argento et al. |
| 2018/0177589 A1 | 6/2018 | Argento et al. |
| 2019/0159890 A1 | 5/2019 | Salahieh et al. |
| 2019/0274823 A1 | 9/2019 | Argento et al. |
| 2019/0290422 A1 | 9/2019 | Ben Nun |
| 2019/0374334 A1 | 12/2019 | Brady et al. |
| 2020/0121447 A1 | 4/2020 | Argento et al. |
| 2020/0306031 A1 | 10/2020 | Salahieh et al. |
| 2020/0397566 A1 | 12/2020 | Salahieh et al. |

FOREIGN PATENT DOCUMENTS

| | | |
|---|---|---|
| AU | 2010203427 | 5/2017 |
| AU | 2012335677 | 6/2017 |
| AU | 2015258287 | 12/2017 |
| CA | 2973684 | 7/2016 |
| CA | 2974639 | 8/2016 |
| CA | 2987311 | 12/2016 |
| CA | 2752046 | 4/2017 |
| CA | 2829143 | 4/2017 |
| CN | 1285722 | 2/2001 |
| CN | 1795090 | 6/2006 |
| CN | 101351169 | 6/2007 |
| CN | 101031257 | 9/2007 |
| CN | 101641060 | 11/2007 |
| CN | 101277659 | 10/2008 |
| CN | 101360468 | 2/2009 |
| CN | 101069106 | 2/2010 |
| CN | 102271623 | 7/2010 |
| CN | 108472129 | 8/2018 |
| CN | 101547663 | 1/2021 |
| EP | 0604369 A1 | 6/1994 |
| EP | 0734269 A1 | 10/1996 |
| EP | 0784652 A1 | 7/1997 |
| EP | 0800511 A1 | 10/1997 |
| EP | 0820601 A1 | 1/1998 |
| EP | 0826158 A1 | 3/1998 |
| EP | 0898972 A2 | 3/1999 |
| EP | 0907668 A1 | 4/1999 |
| EP | 0930357 A1 | 7/1999 |
| EP | 0604369 B1 | 8/1999 |
| EP | 0826158 B1 | 9/1999 |
| EP | 0947856 A2 | 10/1999 |
| EP | 0820601 B1 | 12/1999 |
| EP | 0800511 B1 | 1/2000 |
| EP | 0989138 A2 | 3/2000 |
| EP | 1084428 A1 | 3/2001 |
| EP | 1088246 A1 | 4/2001 |
| EP | 1090313 A1 | 4/2001 |
| EP | 1095711 A2 | 5/2001 |
| EP | 1095965 A1 | 5/2001 |
| EP | 1095966 A2 | 5/2001 |
| EP | 1109853 A1 | 6/2001 |
| EP | 0907668 B1 | 9/2001 |
| EP | 1141054 A1 | 10/2001 |
| EP | 1187873 A1 | 3/2002 |
| EP | 1200019 A1 | 5/2002 |
| EP | 1227773 A1 | 8/2002 |
| EP | 1230041 A2 | 8/2002 |
| EP | 1266246 A1 | 12/2002 |
| EP | 0898972 B1 | 4/2003 |
| EP | 1341485 A1 | 9/2003 |
| EP | 1364663 A1 | 11/2003 |
| EP | 1095711 B1 | 1/2004 |
| EP | 1141054 B1 | 2/2004 |
| EP | 1395302 A1 | 3/2004 |
| EP | 1410074 A1 | 4/2004 |
| EP | 1266246 B1 | 6/2004 |
| EP | 1109853 B1 | 9/2004 |
| EP | 1187873 B1 | 9/2004 |
| EP | 1084428 B2 | 11/2004 |
| EP | 1472305 A1 | 11/2004 |
| EP | 1230041 B1 | 12/2004 |
| EP | 0989138 B1 | 2/2005 |
| EP | 1095965 B1 | 2/2005 |
| EP | 1395302 B1 | 2/2005 |
| EP | 1507811 A1 | 2/2005 |
| EP | 1524953 A2 | 4/2005 |
| EP | 1200019 B1 | 9/2005 |
| EP | 1095966 B1 | 1/2006 |
| EP | 1660153 A2 | 5/2006 |
| EP | 1353611 B1 | 9/2006 |

(56) References Cited

FOREIGN PATENT DOCUMENTS

| | | |
|---|---|---|
| EP | 1696975 A1 | 9/2006 |
| EP | 1341485 B1 | 11/2006 |
| EP | 1723933 A2 | 11/2006 |
| EP | 1723934 A2 | 11/2006 |
| EP | 1750157 A1 | 2/2007 |
| EP | 1088246 B1 | 11/2007 |
| EP | 1857477 A1 | 11/2007 |
| EP | 1227773 B1 | 1/2008 |
| EP | 1888660 A2 | 2/2008 |
| EP | 1890650 A2 | 2/2008 |
| EP | 1902737 A1 | 3/2008 |
| EP | 1723933 B1 | 11/2008 |
| EP | 2035050 A2 | 3/2009 |
| EP | 2035480 A1 | 3/2009 |
| EP | 2035486 A1 | 3/2009 |
| EP | 1723934 B1 | 6/2009 |
| EP | 2066732 A2 | 6/2009 |
| EP | 2077292 A1 | 7/2009 |
| EP | 2092376 A1 | 8/2009 |
| EP | 1648534 B1 | 9/2009 |
| EP | 2094193 A2 | 9/2009 |
| EP | 2109784 A1 | 10/2009 |
| EP | 2120789 A2 | 11/2009 |
| EP | 2126614 A2 | 12/2009 |
| EP | 2035480 B1 | 2/2010 |
| EP | 2170708 A2 | 4/2010 |
| EP | 2185589 A2 | 5/2010 |
| EP | 2231207 A1 | 9/2010 |
| EP | 1750157 B1 | 10/2010 |
| EP | 2235094 A1 | 10/2010 |
| EP | 2276513 A2 | 1/2011 |
| EP | 2292672 A2 | 3/2011 |
| EP | 2356170 A1 | 8/2011 |
| EP | 2356497 A2 | 8/2011 |
| EP | 2109784 B1 | 10/2011 |
| EP | 2396355 A2 | 12/2011 |
| EP | 2035486 B1 | 4/2012 |
| EP | 2452212 A2 | 5/2012 |
| EP | 1857477 B1 | 6/2012 |
| EP | 1410074 B1 | 10/2012 |
| EP | 2092376 B1 | 10/2012 |
| EP | 2510051 A1 | 10/2012 |
| EP | 2513711 A1 | 10/2012 |
| EP | 2514791 A1 | 10/2012 |
| EP | 2356170 B1 | 12/2012 |
| EP | 2538266 A1 | 12/2012 |
| EP | 2563275 A1 | 3/2013 |
| EP | 2597113 A1 | 5/2013 |
| EP | 2598936 A1 | 6/2013 |
| EP | 2077292 B1 | 8/2013 |
| EP | 2625216 A1 | 8/2013 |
| EP | 2625217 A1 | 8/2013 |
| EP | 2625218 A1 | 8/2013 |
| EP | 2652532 A1 | 10/2013 |
| EP | 1830898 B1 | 3/2014 |
| EP | 2766750 A1 | 8/2014 |
| EP | 2452212 B1 | 3/2015 |
| EP | 2934383 A1 | 10/2015 |
| EP | 2200536 B1 | 1/2016 |
| EP | 2976042 A1 | 1/2016 |
| EP | 3185818 | 3/2016 |
| EP | 2129331 B1 | 4/2016 |
| EP | 3003217 A1 | 4/2016 |
| EP | 3025678 A1 | 6/2016 |
| EP | 2259750 B1 | 7/2016 |
| EP | 2934383 A4 | 7/2016 |
| EP | 3062741 A1 | 9/2016 |
| EP | 3072476 A1 | 9/2016 |
| EP | 1999188 B1 | 11/2016 |
| EP | 2685935 B1 | 11/2016 |
| EP | 2094193 | 1/2017 |
| EP | 2683287 | 2/2017 |
| EP | 3062742 | 2/2017 |
| EP | 3157466 | 4/2017 |
| EP | 3160404 | 5/2017 |
| EP | 3160683 | 5/2017 |
| EP | 3049023 | 6/2017 |
| EP | 3160683 | 6/2017 |
| EP | 3174500 | 6/2017 |
| EP | 2539351 | 7/2017 |
| ES | 2283058 T3 | 10/2007 |
| FR | 2653325 A1 | 4/1991 |
| JP | 59-501897 | 11/1984 |
| JP | 01-223970 | 9/1989 |
| JP | 2006-518222 | 8/2006 |
| JP | 2007-506516 | 3/2007 |
| JP | 2007-517616 | 7/2007 |
| JP | 2010-517639 | 5/2010 |
| JP | 2012-532685 | 12/2012 |
| JP | 2016-534816 | 11/2016 |
| WO | 9007545 A2 | 7/1990 |
| WO | 9007575 A1 | 7/1990 |
| WO | 9516475 A1 | 6/1995 |
| WO | 9611235 A1 | 4/1996 |
| WO | 9620919 A1 | 7/1996 |
| WO | 9631791 A1 | 10/1996 |
| WO | 9636890 A1 | 11/1996 |
| WO | 9749740 A1 | 12/1997 |
| WO | 9917684 A1 | 4/1999 |
| WO | 9929818 A1 | 6/1999 |
| WO | 9957581 A1 | 11/1999 |
| WO | 9960428 A1 | 11/1999 |
| WO | 9963366 A1 | 12/1999 |
| WO | 2000004078 A1 | 1/2000 |
| WO | 2000026980 A1 | 6/2000 |
| WO | 2000071613 A1 | 11/2000 |
| WO | 2001008607 A1 | 2/2001 |
| WO | 2001030512 A2 | 5/2001 |
| WO | 2001034067 A1 | 5/2001 |
| WO | 2001071392 A1 | 9/2001 |
| WO | 2002047583 A1 | 6/2002 |
| WO | 2002094331 A1 | 11/2002 |
| WO | 2003009014 A1 | 1/2003 |
| WO | 2003066707 A1 | 8/2003 |
| WO | 2003097711 A1 | 11/2003 |
| WO | 2004010905 A2 | 2/2004 |
| WO | 2004046768 A2 | 6/2004 |
| WO | 2004052242 A1 | 6/2004 |
| WO | 2004053536 A2 | 6/2004 |
| WO | 2004054471 A2 | 7/2004 |
| WO | 2004058318 A1 | 7/2004 |
| WO | 2004072689 A2 | 8/2004 |
| WO | 2005023331 A2 | 3/2005 |
| WO | 2005065734 A1 | 7/2005 |
| WO | 2006047383 A2 | 5/2006 |
| WO | 2006103674 A2 | 10/2006 |
| WO | 2006126095 A2 | 11/2006 |
| WO | 2007005778 A2 | 1/2007 |
| WO | 2007047529 A2 | 4/2007 |
| WO | 2007047530 A2 | 4/2007 |
| WO | 2007050394 A2 | 5/2007 |
| WO | 2007064594 A2 | 6/2007 |
| WO | 2008005644 A1 | 1/2008 |
| WO | 2008005652 A1 | 1/2008 |
| WO | 2008005752 A2 | 1/2008 |
| WO | 2008024766 A2 | 2/2008 |
| WO | 2008039655 A2 | 4/2008 |
| WO | 2008076729 A1 | 6/2008 |
| WO | 2008077040 A2 | 6/2008 |
| WO | 2008082957 A2 | 7/2008 |
| WO | 2008094876 A1 | 8/2008 |
| WO | 2008103798 A2 | 8/2008 |
| WO | 2008107882 A2 | 9/2008 |
| WO | 2008116132 A2 | 9/2008 |
| WO | 2008151088 A2 | 12/2008 |
| WO | 2009002703 A2 | 12/2008 |
| WO | 2020219456 | 12/2008 |
| WO | 2009015161 A2 | 1/2009 |
| WO | 2009015226 A2 | 1/2009 |
| WO | 2009015234 A2 | 1/2009 |
| WO | 2009015240 A2 | 1/2009 |
| WO | 2009085755 A1 | 7/2009 |
| WO | 2009085756 A1 | 7/2009 |
| WO | 2009127844 A2 | 10/2009 |

(56) References Cited

FOREIGN PATENT DOCUMENTS

| | | |
|---|---|---|
| WO | 2010056686 A1 | 5/2010 |
| WO | 2010056687 A2 | 5/2010 |
| WO | 2010081093 A2 | 7/2010 |
| WO | 2010093823 A2 | 8/2010 |
| WO | 2011005937 A2 | 1/2011 |
| WO | 2011026068 A2 | 3/2011 |
| WO | 2011071790 A1 | 6/2011 |
| WO | 2011075377 A1 | 6/2011 |
| WO | 2011106435 A2 | 9/2011 |
| WO | 2012006616 A2 | 1/2012 |
| WO | 2012015639 A1 | 2/2012 |
| WO | 2012047961 A1 | 4/2012 |
| WO | 2012047964 A1 | 4/2012 |
| WO | 2012047969 A1 | 4/2012 |
| WO | 2012082704 A1 | 6/2012 |
| WO | 2012129407 A2 | 9/2012 |
| WO | 2021007535 | 9/2012 |
| WO | 2012129419 | 4/2013 |
| WO | 2013055746 A1 | 4/2013 |
| WO | 2013070924 A1 | 5/2013 |
| WO | 2013158942 A1 | 10/2013 |
| WO | 2013166068 A1 | 11/2013 |
| WO | 2014093751 A2 | 6/2014 |
| WO | 2014093764 A1 | 6/2014 |
| WO | 2014095690 A1 | 6/2014 |
| WO | 2014099630 A1 | 6/2014 |
| WO | 2014143926 A1 | 9/2014 |
| WO | 2014149462 A1 | 9/2014 |
| WO | 2014152017 A1 | 9/2014 |
| WO | 2015038620 A2 | 3/2015 |
| WO | 2015048279 A1 | 4/2015 |
| WO | 2015066502 A1 | 5/2015 |
| WO | WO2015066532 | 5/2015 |
| WO | 2015148673 A1 | 10/2015 |
| WO | 2016018932 | 2/2016 |
| WO | 2016018932 A1 | 2/2016 |
| WO | 2016033217 A1 | 3/2016 |
| WO | 2016038470 A2 | 3/2016 |
| WO | 2016061233 A1 | 4/2016 |
| WO | 2016122805 A1 | 8/2016 |
| WO | 2016133558 | 8/2016 |
| WO | 2016140708 A1 | 9/2016 |
| WO | 2016195095 A1 | 12/2016 |
| WO | 2016201351 A1 | 12/2016 |
| WO | 2013059195 | 5/2017 |
| WO | 2017079449 | 5/2017 |
| WO | 2017079733 | 5/2017 |
| WO | 2017087358 | 5/2017 |
| WO | 2009002789 | 12/2017 |
| WO | 2017208230 | 12/2017 |
| WO | 2017223544 | 12/2017 |
| WO | 2018119408 | 6/2018 |
| WO | 2017221196 | 8/2018 |
| WO | 2018222579 | 12/2018 |
| WO | 2018227014 | 12/2018 |

OTHER PUBLICATIONS

Tsao, et al. "Bonding of thermoplastic polymer microfluidics. Microfluid Nanofuild," 2009, 6:1-16.

Umbrecht, et al. "Solvent assisted bonding of polymethylmethacrylate: characterization using the response surface methodology," 2008, pp. 1325-1328.

Liang et al., "Bionic intraocular lens with variable focus and integrated structure," Optical Engineering 2015, vol. 54, No. 10, Article No. 105106, Internal pp. 1-7.

International Search Report and Written Opinion for PCT Application No. PCT/US2018/036548, filed Jun. 7, 2018, Applicant: Shifamed Holdings, LLC, dated Aug. 30, 2018, 8 pages.

First Chinese Office Action dated Sep. 10, 2020 for Chinese Patent Application No. 201780087361.6, Applicant: Shifamed Holdings, LLC, filing date: Dec. 23, 2017, 11 pages.

International Search Report and Written Opinion for PCT Application No. PCT/US2020/029131, filed Apr. 21, 2020, Applicant: Shifamed Holdings, LLC, dated Sep. 21, 2020, 15 pages.

International Search Report and Written Opinion for PCT Application No. PCT/US2020/041644, filed Jul. 10, 2020, Applicant: Shifamed Holdings, LLC, dated Oct. 27, 2020, 11 pages.

European Extended Search Report dated Jan. 27, 2021 for European Patent Application No. 18809676.2, Applicant: Shifamed Holdings, LLC, filing date: May 29, 2018, 8 pages.

Chinese Office Action dated Jun. 3, 2021 for Chinese Patent Application No. 201880050631.0, Applicant: Shifamed Holdings, LLC, 7 pages.

Chinese Office Action dated Feb. 7, 2021 for Chinese Patent Application No. 201680079359.X, Applicant: Shifamed Holdings, LLC, 8 pages.

International Search Report and Written Opinion for PCT Application No. PCT/US2021/016760, filed Feb. 5, 2021, Applicant: Shifamed Holdings, LLC, dated Jun. 9, 2021, 14 pages.

Chinese Office Action dated Aug. 20, 2021 for Chinese Patent Application No. 201910547059.5, Applicant: Shifamed Holdings, LLC, 10 pages.

\* cited by examiner

ADJUSTABLE OPTICAL POWER INTRAOCULAR LENSES

CROSS-REFERENCE TO RELATED APPLICATION(S)

This application is a 35 U.S.C. § 371 U.S. National Phase application of International Patent Application No. PCT/US2018/036548, filed Jun. 7, 2018, and entitled ADJUSTABLE OPTICAL POWER INTRAOCULAR LENSES, which claims priority to U.S. Provisional Application No. 62/516,541, filed Jun. 7, 2017, and entitled ADJUSTABLE INTRAOCULAR LENS, the contents of each of the above applications are incorporated herein by reference in their entireties.

Intraocular lenses (IOLs) are implantable optical devices for treating cataracts or myopia. IOLs typically replace native crystalline lenses that are cloudy or otherwise discolored due to cataracts. An IOL is surgically implanted by removing the native crystalline lens and then inserting an IOL into the native lens capsule. The World Health Organization estimates that 20 million IOLs were implanted worldwide in 2010 and predicts that 30 million IOLs will be implanted annually by 2020.

BACKGROUND

Many current IOLs have a single optical power that is set by the manufacturer. As a result, conventional single-power IOLs have a fixed optical power. This requires practitioners to determine the optical power of single-power IOLs before implantation. The optical power of an IOL, however, may not be correct after implantation because the IOL may not fit properly in the native lens capsule or the eye may change over time. If the optical power of an implanted single-power IOL is not correct, the IOL will need to be replaced with another IOL having a suitable optical power via another surgical procedure. This not only increases the cost of healthcare, but it is also inconvenient for the patients and subject to the normal complications of optical surgical procedures.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

OVERVIEW

Figure 1:
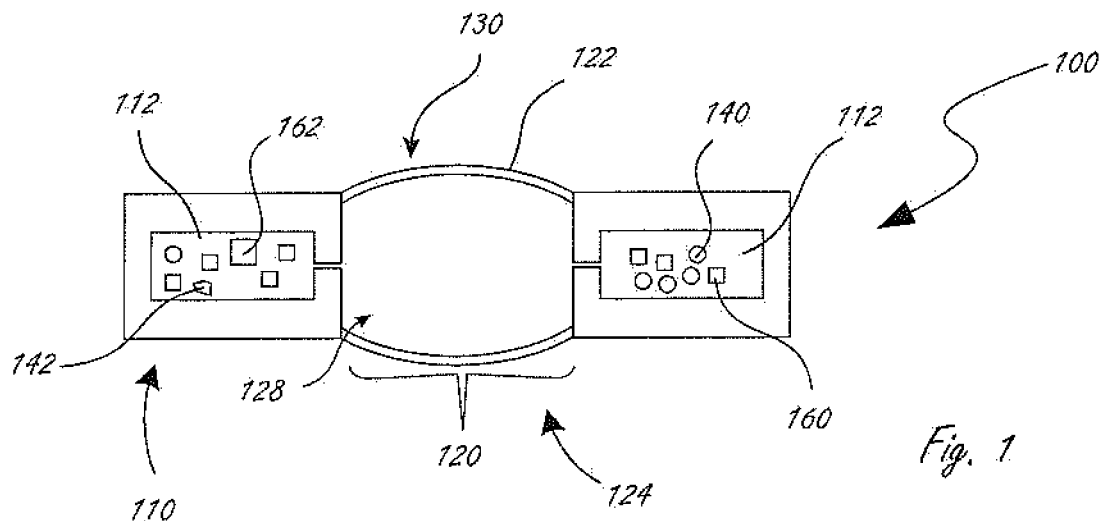
FIG. 1 is a cross-sectional view of an adjustable power intraocular lens in accordance with the present technology.

Several embodiments of adjustable power intraocular lenses (APIOLs) in accordance with the present technology are described below with reference to FIGS. 1-8. The APIOLs described below are capable of changing the optical power in situ using a non-invasive activation. Although several examples of APIOLs are disclosed with respect to single-power devices, the concept can be applied to accommodating intraocular lenses as well as noted below.

The disclosed APIOLs provide the ability to selectively change the optical power in situ to adapt the APIOLs to the specific power required by the patient after implantation without removing and/or replacing the APIOLs. For example, several embodiments of APIOLs in accordance with the present technology include first volume control elements that release or expel a transport substance and/or second volume control elements that absorb or otherwise attract and retain a transport substance. The first volume control elements can be shrinking elements or release elements configured to release the transport substance upon non-invasive activation, such as an energy modality that selectively reacts with the first volume control elements. Conversely, the second volume control elements can be swelling elements configured to absorb or otherwise attract and retain the transport substance upon non-invasive activation. In operation, the shrinking elements can be activated to release the transport substance from the APIOL to reduce the optical power, or conversely the swelling elements can be activated to absorb the transport substance to increase the optical power.

APIOLs in accordance with present technology can include a container, an optical fluid in the container, and volume control elements in the container. The container can comprise a peripheral component and an optical component. The optical component, for example, can include an anterior optical element and a posterior optical element. The optical elements may be hydrophilic or hydrophobic. The container can comprise a water permeable material. One suitable water permeable material for the container comprises:
  a—a hydrophilic acrylic copolymer;
  b—Benz 25 UVX™ material manufactured by Benz Research and Development of Sarasota, Fla.; and
  c—CI18, CI21, or CI26 produced by Contamac Ltd. of the UK Suitable hydrophilic acrylics include, but are not limited to, 2-Hydroxyethyl methacrylate (HEMA). Suitable hydrophobic acrylics include, but are not limited to, 2-Ethoxyethyl methacrylate (EOEMA), polymethyl methacrylate (PMMA), Butyl acrylate, Hexyl acrylate and Hexafluoroisopropyl acrylate. The acrylic, for example, can comprise a cross linker. In some embodiments, the acrylic comprises a cross-linked acrylic polymer. The hydrophilic or hydrophobic polymers may be copolymers of the above.

The internal optical fluid filling the container can comprise an oil. For example, the oil can have a refractive index greater than that of the aqueous humor. The oil can be capable of holding a saturation volume of water in solution at body temperatures of a human eye. The transport substance can be water.

The volume control elements can include first volume control elements configured to release a transport substance into the optical fluid in the container and/or second volume control elements configured to absorb a transport substance from the optical fluid. The first volume control elements can be shrinking elements that, when activated, release the transport substance into the optical fluid and thereby increase the volume of the transport substance in the fluid chamber. This causes the transport substance concentration within the container to exceed the saturation point such the transport substance is transported out of the container to the aqueous humor by diffusion. The reduction in the transport substance reduces the volume of matter in the container, which in turn reduces the optical power of the optical component. The second volume control elements can be swelling elements that, when activated, absorb the transport substance from the optical fluid. This too causes an imbalance of the transport substance within the container such that additional transport substance is transported from the aqueous humor into the container via diffusion. The increase in the transport substance increases the volume of matter in the container, which in turn increase the optical power of the optical component.

The first volume control elements, or shrinking elements, can include a first hydrophobic casing containing a volume of the transport substance. For example, the transport substance can be water and the first hydrophobic casing can be wax or a liposome (e.g., a uni-laminar liposome). In one example, the first volume control elements can be wax closed-cell foams containing water.

The second volume control elements, or swelling elements, can include one or more hydrophilic elements surrounded by a second hydrophobic casing. The hydrophilic elements can include a hydrogel such as acrylic polymers. The second hydrophobic casing can include parylene and/or a hydrophobic acrylic.

The first and/or second volume control elements can be fixed to the container. In other embodiments, the first and/or second volume control elements can be suspended in the optical fluid.

The optical component of APIOLs in accordance with the present technology can be a fluid lens comprising the optical fluid (e.g., oil) bounded by the anterior optical element and the posterior optical element. The peripheral component can surround the optical component such that the optical component is a central portion of the container. In some embodiments, one or both of the anterior and posterior optical elements may have an optical power (i.e., a defined curvature in a relaxed unbiased state) such that the optical component has an optical power in a relaxed state. In other embodiments, the anterior and/or posterior optical elements may be flat membranes that have no optical power in a relaxed unbiased state such that the optical component has no power in the relaxed state. The total volume of the optical fluid, transport substance and first and/or second volume control elements within the container can change the curvature, and thus the optical power, of the optical component. More specifically, the optical power increases when the volume of matter within the container increases, or conversely the optical power decreases when the volume of matter within the container decreases.

The volume of matter within the container is controlled by selectively activating the first volume control elements or the second volume control elements. The first or second volume control elements can be activated by disrupting all or a portion of the hydrophobic casings of the volume control elements. For example, in several embodiments the volume control elements are activated by exposing the volume control elements to a non-invasive activation energy that selectively disrupts either the first hydrophobic casings of the first volume control elements or the second hydrophobic casings of the second volume control elements. The non-invasive activation energy can include laser energy (e.g., light), ultrasound, electrical energy (e.g., radio frequency), and/or infrared.

DETAILED DESCRIPTION

FIG. 1 is a cross-sectional view schematically illustrating an APIOL 100 having a peripheral component 110 and an optical component 120. The peripheral component 110 and the optical component 120 together can define a container, or just the peripheral component can define the container. The peripheral component 110 can be an annular outer compartment that completely surrounds the optical component 120, or the peripheral component 110 can be discrete outer segments that extend around only a portion of the optical component 120. The peripheral component 110 can have interior volume 112 that is in fluid communication with the optical component 120. In other embodiments, however, the interior volume 112 of the peripheral component 110 can be fluidically isolated from the interior of the optical component 120. The peripheral component 110 can be stiffer than the optical component 120 such that changes in volume occur to a greater in the optical component 120 than in the peripheral component 110.

The optical component 120 can have an anterior optical element 122 coupled to an anterior portion of the peripheral component 110, a posterior optical element 124 coupled to a posterior portion of the peripheral component 110, and a fluid chamber 126 between the anterior optical element 122 and the posterior optical element 124. The anterior optical element 122 can be a first membrane, and the posterior optical element 124 can be a second membrane. The first and second membranes can have an optical power (e.g., have a set or minimum curvature) or they can have no optical power in a relaxed, unbiased state (e.g., horizontal in FIG. 1). The fluid chamber 126 can be filled with an optical fluid 128 such that the anterior optical element 122, the posterior optical element 124 and the optical fluid define a fluid lens 130. In operation the optical fluid 128 can fill both the peripheral component 110 and the fluid chamber 126 to impart the desired curvature to the anterior optical element 122 and/or the posterior optical element 124 to provide the desired optical power to the optical component 120. The optical component 120 can have a single power or it can be an accommodating fluid lens in which the optical power changes in response to movement of the muscles of the native eye.

The APIOL 100 can further include first volume control elements 140 and/or second volume control elements 160. The first volume control elements 140 can be shrinking elements or release elements configured to disgorge or otherwise release a transport substance using a first non-invasive activation modality. Conversely, the second volume control elements 160 can be swelling elements configured to absorb or otherwise attract and retain a substance using a second non-invasive activation modality. The first and second non-invasive activation modalities can be one or more types of energy, such as laser radiation, ultrasonic energy, radio frequency (RF) energy or infrared radiation, that selectively activates one or both of the first and second volume control elements 140 and 160. In several embodiments, the first non-invasive activation modality activates only the first volume control elements 140 and the second non-invasive activation modality activates only the second volume control elements 160 such that the first and second volume control elements 140 and 160 can be activated independently of each other. For example, the first volume control elements 140 can be activated by one type of energy (e.g., laser energy), while the second volume control elements 160 can be activated by a different type of energy (e.g., RF energy). In a different example, the first and second volume control elements 140 and 160 can be activated by a common type of energy at different wavelengths or frequencies. In this example the first volume control elements 140 can be activated by a type of energy at a first wavelength or frequency (e.g., laser energy in a first bandwidth) and the second volume control elements 160 can be activated by the same type of energy at a second wavelength or frequency (e.g., laser energy in a second bandwidth). The second bandwidth is sufficiently different than the first bandwidth to avoid joint activation of the first and second volume control elements. In other embodiments, a single non-invasive activation modality can activate both the first volume control elements 140 and the second volume control elements 160. Upon activation, the first and second volume control elements 140 and 160 can become first and second activated elements 142 and 162, respectively.

The optical fluid 128 and the transport substance (not shown in FIG. 1) are selected to maintain a desired equilibrium within the fluid chamber 126 with respect to the aqueous humor of the native eye. The transport substance is selected to transport through the walls of the peripheral component 110, the anterior optical element 122, and/or the posterior optical element 124 via osmosis to maintain the desired equilibrium between the optical fluid 128 and the transport substance within the fluid chamber 126. In several embodiments, the optical fluid 128 is an oil that can sustain a solubilized water content of greater than a few percent and the transport substance is water. As a result, the first volume control elements 140 (e.g., shrinking elements) provide a water source within the APIOL 100, whereas the second volume control elements 160 (e.g., swelling elements) provide a sink for water. As the internal volume is a changed by activating either the first volume control elements 140 elements or the second volume control elements 160, the volume of the matter in the fluid chamber 126 changes and thereby adjusts the power of the optical component 120 in situ. In general, when the internal volume of matter in the fluid chamber 126 increases the optical power increases, and conversely when the internal volume of matter in the fluid chamber 126 decreases the optical power decreases.

Figure 2:
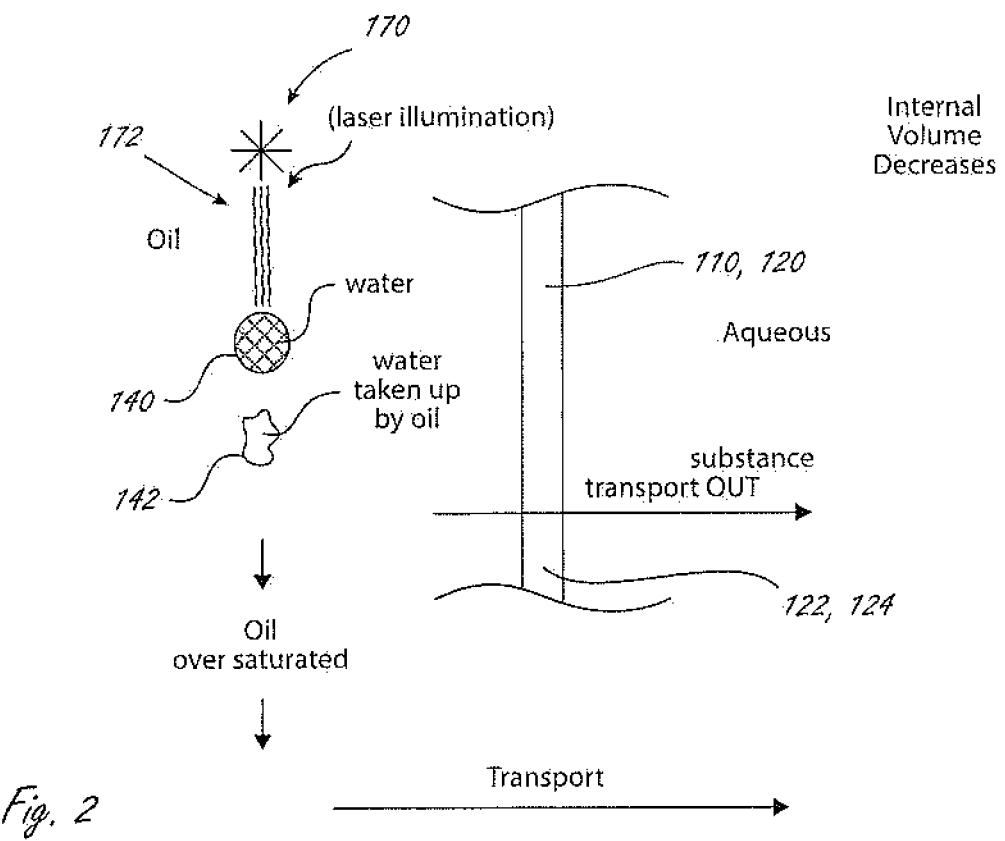
FIGS. 2 and 3 are cross-sectional views of the operation of first and second volume control elements, respectively, used in adjustable power intraocular lenses in accordance with the present technology.

FIG. 2 schematically illustrates the operation of the first volume control elements 140, and more specifically releasing or expelling the transport substance (e.g., water) from the first volume control elements 140 to reduce the optical power of the optical component 120. In this aspect of the present technology, an energy source 170 produces a non-invasive activation energy 172 that interacts with the first volume control elements 140 such that the first volume control elements 140 release or otherwise expel the transport substance. As the transport substance is released from the first volume control elements 140, the transport substance over-saturates the internal fluid or optical fluid 128 within the APIOL 100. The excess transport substance passes through the wall of the peripheral component 110 and/or the optical elements 122, 124 of the optical component 120 into the surrounding aqueous humor. The internal volume of the APIOL 100 is therefore reduced by the volume of transport substance that transports out of the APIOL 100. Since the peripheral component 110 of the APIOL 100 is structurally stiffer than the optical component 120, the volume of the optical component 120 changes more than that of the peripheral component 110. The decrease in volume of the optical component 120 decreases the optical power of the optical component 120.

Figure 3:
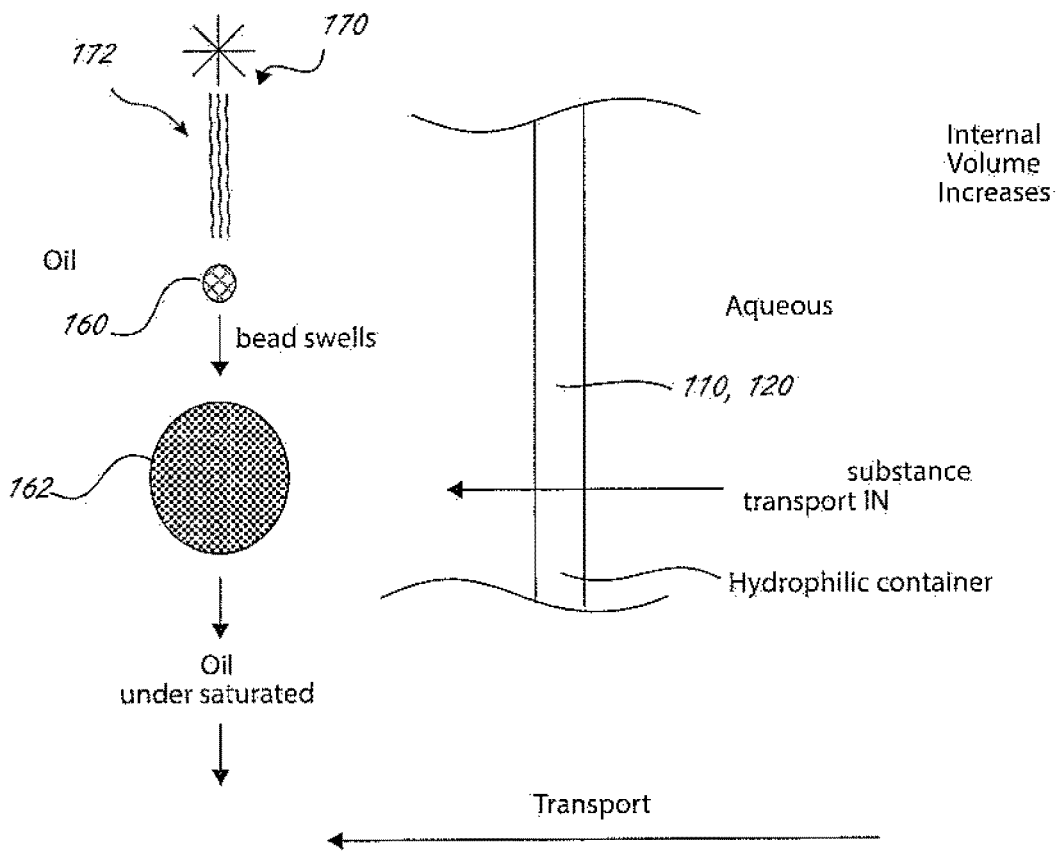

FIG. 3 schematically illustrates the operation of the second volume control elements 160, and more specifically absorbing or otherwise collecting the transport substance (e.g., water) in and/or on the second volume control elements 160 to increase the optical power of the optical component 120. In a specific example of the present technology, the optical power of the APIOL 100 increases by the sequestration of water into the second volume control elements 160. More specifically, the transport substance is absorbed into the second volume control elements 160 from the optical fluid, and the second volume control elements 160 swell to occupy more volume. The transport substance removed from the optical fluid is replaced by the same type of substance from the aqueous humor which passes through the peripheral component 110 and/or the optical component 120 from the surrounding aqueous humor into the optical fluid. This brings the chemistry of the optical fluid back to its equilibrium level (e.g., water:oil equilibrium ratio). The internal volume of the APIOL 100 is therefore increased by the volume of water which has been absorbed into the second volume control elements 160 within the APIOL 100. Since the peripheral component 110 of the APIOL 100 is structurally stiffer than the optical component 120, the volume of the optical component 120 increases and thereby increases the optical power of the optical component 120.

Figure 4:
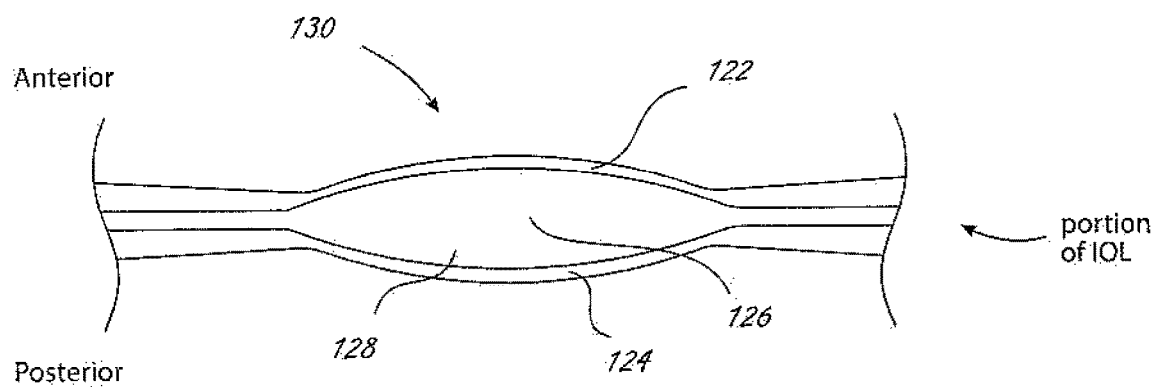
FIG. 4 is a cross-sectional view of an adjustable power intraocular lens in accordance with the present technology.

FIG. 4 is a cross-sectional view illustrating aspects of the optical component 120 in greater detail. The anterior optical element 122 and the posterior optical element 124 can define a container or structural portion of the APIOL 100. As illustrated, both membranes are thin and flat in a relaxed unbiased state (e.g., plate-like) and provide no optical power to the optical component 120 in this state. As the internal volume of the APIOL 100 increases, the membranes flex into roughly spherical curvatures. The high refractive index optical fluid 128 between the membranes, in combination with the optical elements 122 and 124, thereby forms the fluid lens 130 which has an optical power. The optical power of the fluid lens 130 increases as the volume of the optical fluid 128 in the fluid chamber 126 increases. In other embodiments (not shown), one or both the anterior optical element 122 and the posterior optical element 124 may have a curvature in a relaxed unbiased state such that they comprise an optical power. In still other embodiments, one of the anterior optical element 122 or posterior optical element 124 may be stiffer and or thicker than the other (not shown).

Figure 5:
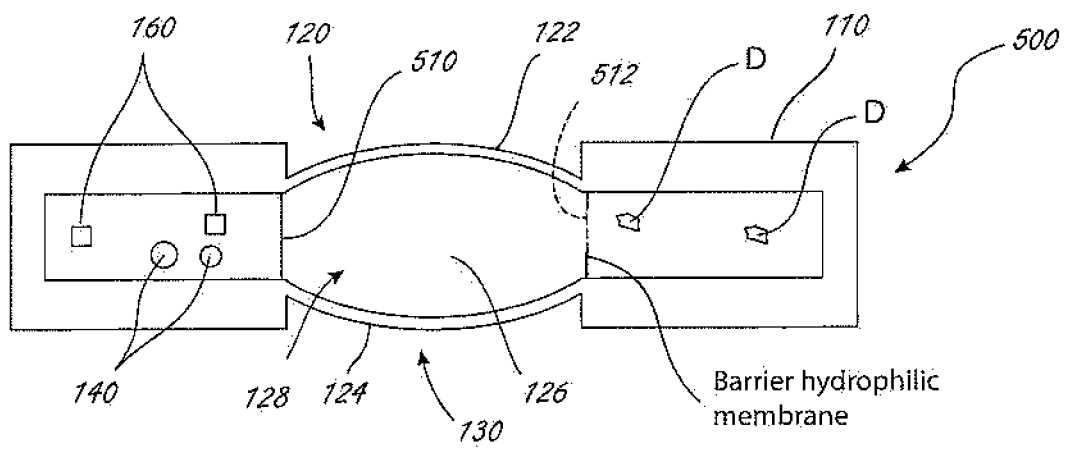
FIG. 5 is a cross-sectional view of an adjustable power intraocular lens in accordance with the present technology.

FIG. 5 illustrates an APIOL 500 in accordance with the present technology. The APIOL 500 is similar to the APIOL 100 described above, and like reference numbers refer to like components. The APIOL 500 is different than the APIOL 100 in that the peripheral component 110 and the optical component 120 of the APIOL 500 are fluidically isolated from each other by a barrier 510. The barrier 510, for example, can be a hydrophilic membrane. In such an embodiment, the barrier 510 constrains debris ("D") associated with the activation of the first and/or second volume control elements 140, 160 from entering the fluid chamber 126 of the optical component 120. In some such embodiments, the membrane 510 may be continuous between the peripheral component 110 and the optical component 120, as illustrated in FIG. 5. Whereas in other embodiments the membrane 510 may contain channels or large pores 512 (shown in dotted line) which prevent or otherwise inhibit the debris D from passing into the optical component 120 while allowing the optical fluid 128 to pass to/from the fluid chamber 126. This embodiment is expected to be useful for providing an adjustable accommodating fluid lens in which the optical component 120 increases/decreases optical power as the native eye acts upon the peripheral component 110 to pump fluid into or withdraw fluid out to the fluid chamber 126 (see, e.g., International Application No. [Insert 120974.8012WO00], which is incorporated herein by reference).

Figure 6:
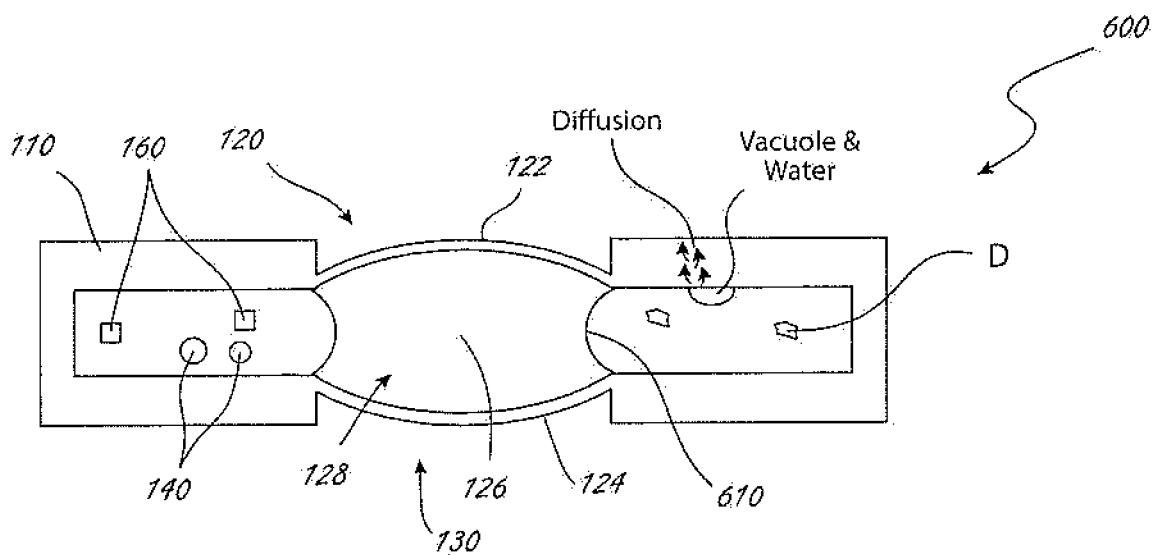
FIG. 6 is a cross-sectional view of an adjustable power intraocular lens in accordance with the present technology.

FIG. 6 is a cross-sectional view illustrating an APIOL 600 in accordance with the present technology in which the optical component 120 is surrounded by a deformable barrier 610. The APIOL 600 is similar to the APIOLs 100 and 500 described above, and like reference numbers refer to like components. The fluid in the peripheral component 110, which includes the first and second volume control elements 140, 160, acts on the deformable barrier 610. In some embodiments, the deformable barrier 610 is bellows. In operation, the optical fluid 128 may have a more standard low solubility for water, and vacuoles of water released from the first volume control elements 140 diffuse to the outer surfaces of the peripheral component 110 that communicate with the aqueous humor.

Figure 7:
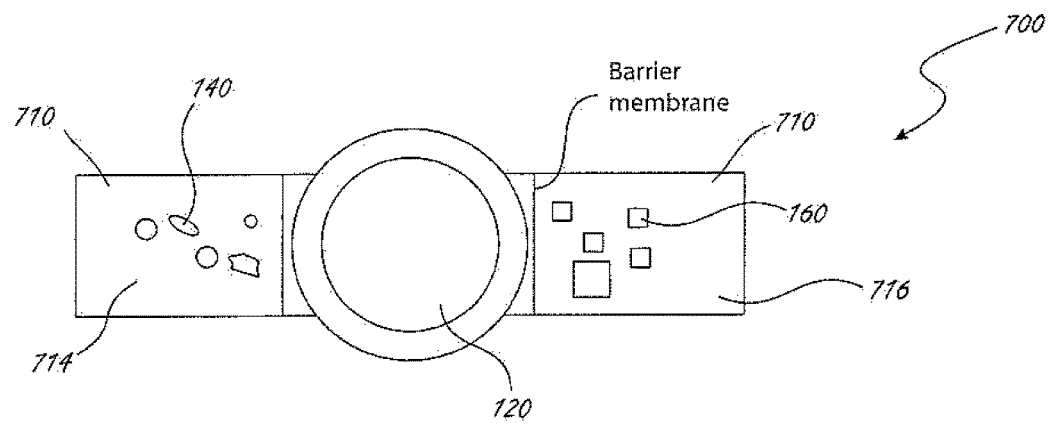
FIG. 7 is a plan view of an adjustable power intraocular lens in accordance with the present technology.

FIG. 7 is a plan view of an APIOL 700 in accordance with the present technology in which like reference numbers refer to like components with respect to FIGS. 1-6. The APIOL 700 has a peripheral component 710 and the optical component 120 in the center of the peripheral component 710. The peripheral component 710 has a first compartment 714 containing a fluid and the first volume control elements 140, and the peripheral component 710 has a second compartment 716 containing a fluid and the second volume control elements 160. The APIOL 700 accordingly differs from the APIOLs 100, 500 and 600 in that the first volume control elements 140 are isolated from the second volume control elements 160 in the first and second compartments 714 and 716, respectively.

Figure 8A:
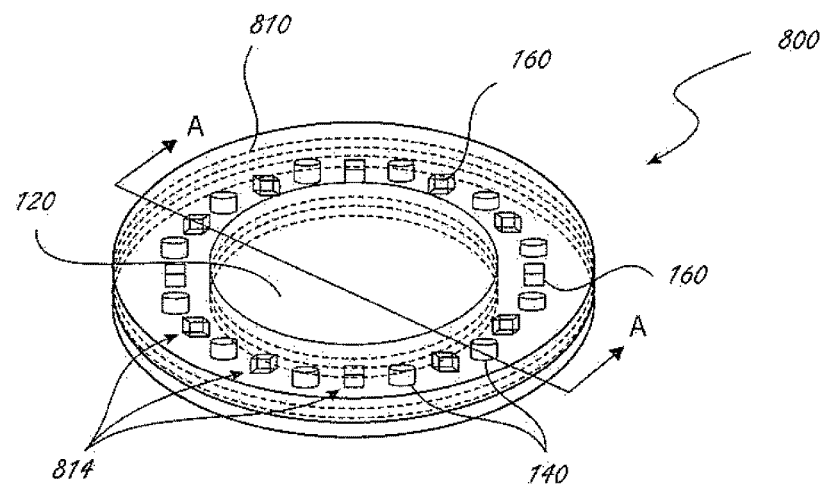
FIG. 8A is an isometric view and FIG. 8B is a cross-sectional view taken along section A-A of FIG. 8A of an adjustable power intraocular lens in accordance with the present technology.
Figure 8B:
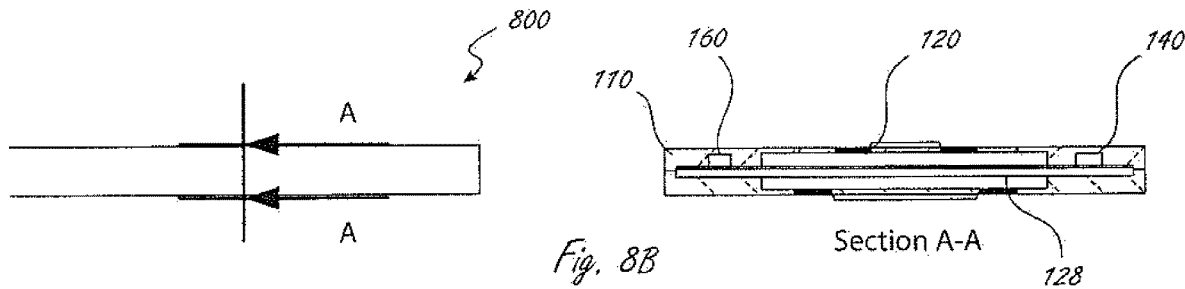

FIG. 8A is an isometric view and FIG. 8B is a cross-sectional view taken along section A-A of FIG. 8A of an APIOL 800 in accordance with the present technology. The APIOL 800 also isolates the first volume control elements 140 from the second volume control elements 160, but the APIOL 800 uses multiple compartments. More specifically, the APIOL 800 has a peripheral component 810 that completely surrounds the optical component 120, and the peripheral component 810 has a plurality of first compartments 814 configured to contain separate volumes of the first volume control elements 140 and a plurality of second compartments 816 configured to contain separate volumes of the second volume control elements 160. Each of the APIOLs 700 and 800 can have a connecting barrier between the compartments containing the volume control elements and the optical component 120. In such embodiments, deformation of the connecting barrier driven by activation of the volume control elements 140, 160 adjusts the peripheral volume of the optical component 120 of the APIOLs 700 and 800.

The first volume control elements 140 can have a thin outer wall and a volume of the transport substance within the thin outer wall. For example, the first volume control elements 140 can have a thin wax shell and a small volume of water encased within the shell. In other embodiments, the first volume control elements 140 can have water encased by a liposome shell, such as a uni-laminar liposome shell having of a bilayer lipid outer membrane. In other embodiments, the first volume control elements 140 can be a closed-cell wax foam with water in the voids of the closed-cell foam.

The second volume control elements 160 can comprise of an outer surface of hydrophobic material encasing either a hydrophilic material or a material which can diffuse or otherwise pass through the optical fluid 128 and/or some portion of the peripheral wall of the APIOL. For example, the second volume control elements 160 described herein can include a small volume of a dehydrated hydrogel encased in a thin layer of wax, a parylene coating, or a layer of an amphiphilic material such that the hydrophilic head groups are presented as the outer surface of the hydrogel and the hydrophobic tail groups are presented outwardly to the environment forming a micelle. The second volume control elements 160 can also be a closed-cell wax foam wherein the voids within the foam contain hydrogel.

The volume control elements 140, 160 described above can be activated by controllably disrupting the shells or outer coating layers thereby allowing a controlled amount of the contained material to access the local environment. Such energy may be one or any combination of laser energy, ultrasound, electrical energy including RF, and infrared energy. In some embodiments, the disruption is accomplished by the delivery of laser energy to the volume control elements. In some embodiments, the first volume control elements 140 and the second volume control elements 160 are activated by different wavelengths of laser energy or different frequencies of ultrasonic or electrical energies. For example, a first wavelength of laser energy is used to activate the first volume control elements 140, while a second different wavelength of laser energy is used to activate the second volume control elements 160. Such selectivity may be built into the volume control elements by controlling the absorbance of the coating material and or the size of the volume control element. In alternative embodiments, the first and second volume control elements 140, 160 may be compartmentalized such that they can be addressed separately as described above with reference to FIGS. 7, 8A and 8B.

Figure 9A:
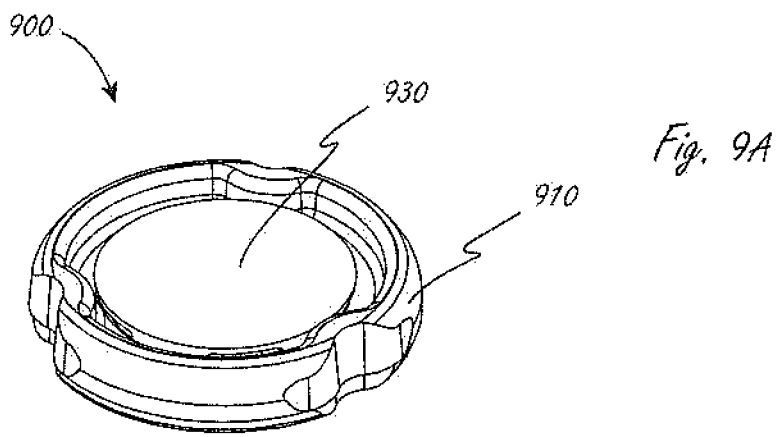
FIG. 9A is an isometric view.
Figure 9B:
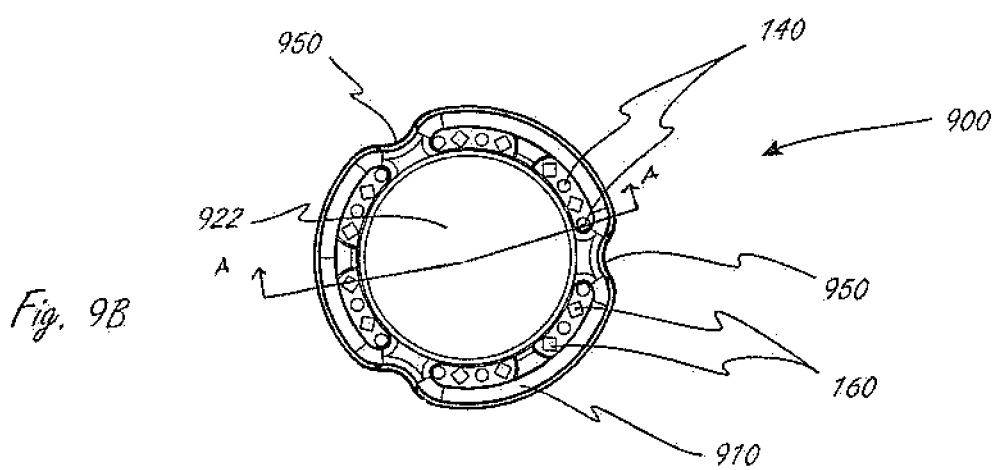
FIG. 9B is a bottom plan view.
Figure 9C:
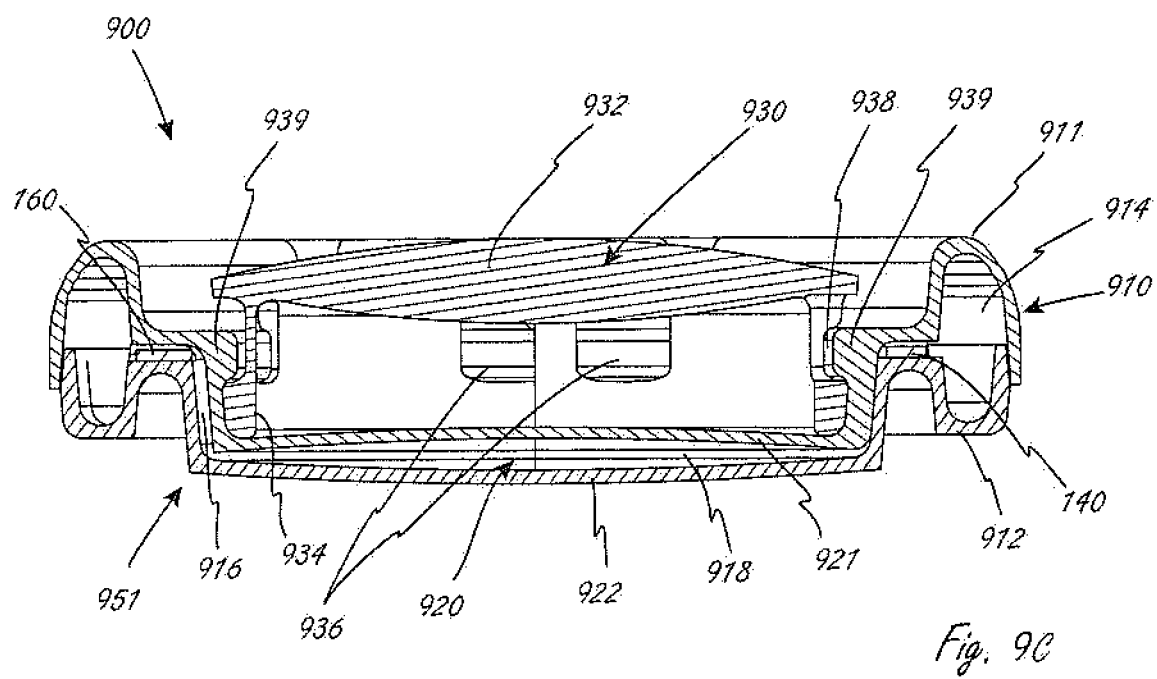
FIG. 9C is a cross-sectional view taken along cross-section A-A of FIG. 9B that illustrate a modular APIOL in accordance with the present technology.

FIG. 9A is an isometric view, FIG. 9B is a bottom plan view, and FIG. 9C is a cross-sectional view taken along cross-section A-A of FIG. 9B that illustrate a modular APIOL 900 in accordance with the present technology. Referring to FIGS. 9A and 9B, the APIOL 900 has an accommodation structure 910, a fixed lens 930, first volume control elements 140, and second volume control elements 160. Referring to FIG. 9C, the accommodating structure 910, for example, can have a first component 911 defining an anterior portion and a second component 912 defining a posterior portion. The first and second components 911 and 912 are assembled to form an outer fluid reservoir 914, a channel 916, and an inner fluid chamber 918 in fluid communication with each other. The outer fluid reservoir 914, channel 916 and inner fluid chamber 918 are filled with an optical fluid and transport substance in solution, which flow between the outer fluid reservoir 914 and the inner chamber 918 via the channel 916.

The accommodating structure 910 can have an accommodating optical element 920 (e.g., an accommodating fluid lens) having a first optical component 921 defining an anterior side of the inner fluid chamber 918 and a second optical component 922 defining a posterior side of the inner fluid chamber 918. The first and second optical components 921 and 922 can be flexible membranes that do not have an optical power, or in other embodiments one or both of the first and second components 921 and 922 can be flexible lenses that have an optical power. In operation, fluid flows between the outer fluid reservoir 914 and the inner chamber 918 in response to the movement of the ciliary muscles of the native eye. For example, when the ciliary muscles relax, the capsular bag pushes against the outer fluid reservoir 914, which in turn causes fluid to flow into the inner chamber 918 and deflect the first optical component 921 anteriorly. This increases the thickness of the accommodating optical element 920. Conversely, when the ciliary muscles contract, the capsular bag is pulled radially outward such that the force exerted against the outer fluid reservoir 914 decreases allowing the higher-pressure fluid in the inner chamber 918 to flow into the outer fluid reservoir 914. This decreases the thickness along the optical axis (e.g., curvature) of the accommodating optical element 920.

The APIOL 900 includes flow-through features 950 that enhance the rate and ease with which Ophthalmic Viscosurgical Devices (OVDs) used during the implantation of AIOLs can be removed from the natural lens capsule. The APIOL 900 can have three outer flow-through features 950. The outer flow-through features 950 can be detents, such as a recess, distributed circumferentially along the perimeter of the outer fluid reservoir 914. In the illustrated embodiment, the flow-through features 950 are formed in regions of the first and second components 911 and 912. Although three outer flow-through features 950 are illustrated, other embodiments may comprise less or more than illustrated. The outer flow-through features 950 may additionally constrain rotation of the APIOL 900 in the eye.

The APIOL 900 additionally comprises a fixed lens assembly 930. The fixed lens assembly 930 illustrated in FIG. 9C includes an optical portion 932, a skirt 934 extending from the optical portion 932, and passages 936. The optical portion 932 has a fixed power which may comprise an asymmetrically powered lens or other lens as explained herein, and the passages 936 are holes, slots, orifices, etc., that pass through the skirt 934 and extend into a perimeter region but not the optical portion 932.

Referring to FIG. 9C, the fixed lens assembly 930 has an engagement feature 938, such as an annular groove, that extends around the skirt 934, and the first component 911 of the accommodating structure 910 has a thickened region 939, such as an annular protrusion (e.g., a ledge) that extends radially inwardly. The fixed lens assembly 930 can be attached to the accommodating structure 910 by engaging the continuous thickened region 939 of the first component 910 with the engagement feature 938 of the fixed lens assembly 930. In other embodiments (not shown), the thickened region 939 and the engagement feature 938 may be discontinuous features (e.g., segmented or other recesses or protrusions that extend around less than the full circumference of the fixed lens assembly 930 and the accommodating structure 910). Such a discontinuous thickened region 939 and engagement feature 938 are desirable to maintain a particular radial alignment between the fixed lens assembly 930 and the accommodating structure 910, such as when the fixed lens assembly 930 comprises a toric lens or other asymmetrical lens. Alternatively, the groove may be in the fixed lens assembly 930 and the protrusion on the accommodating structure 910.

The fixed lens assembly 930 can be implanted after the accommodating portion 910 has been implanted. This is expected to be advantageous because the accommodating portion 910 can be implanted and then a fixed lens assembly 930 with the desired power can be selected and implanted later based on the actual post-implant optical power of the accommodating portion 910. The fixed lens assembly 930 can also be removed after being attached to the accommodating structure 910. This is advantageous if the fixed lens assembly 930 that was initially implanted is not correct or was damaged while being inserted into the accommodating structure 910.

The APIOL 900 can further include a square-shaped annular region 951 that inhibits cell migration from the periphery of the patient's capsule to the optical part of APIOL 900 (shown in FIG. 9C at the posterior most region of the lens). Such cell migration could cause post-surgery opacification of the optical system.

Referring to FIGS. 9B and 9C, the APIOL 900 includes the first and second volume control elements 140 and 160 in the outer fluid reservoir 914. As a result, when the first or second volume control elements 140 or 160 are activated, the volume of matter in the outer fluid reservoir 914 decreases or increases, respectively, as described above. The change in volume of matter in the outer fluid reservoir 914 accordingly changes the volume in the accommodating optical element 920, which in turn adjusts the power of the APIOL 900 as described above. This is expected to be useful even in the APIOL 900 that has a removable fixed lens assembly 930. For example, even though the fixed lens assembly 930 can be implanted after the accommodating structure 910 has been implanted or removed if not appropriate, activating the first or second volume control elements 140 or 160 can be used to further adjust the optical power of the APIOL 900 if needed.

Figure 10A:
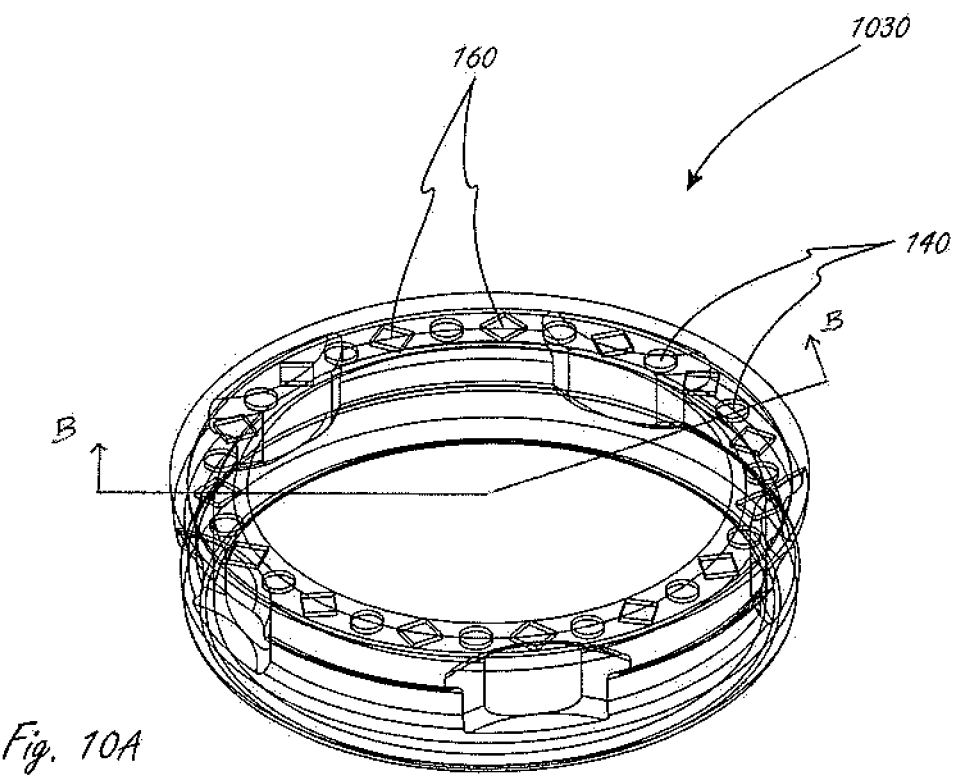
FIG. 10A is a bottom isometric view of a fixed lens.
Figure 10B:
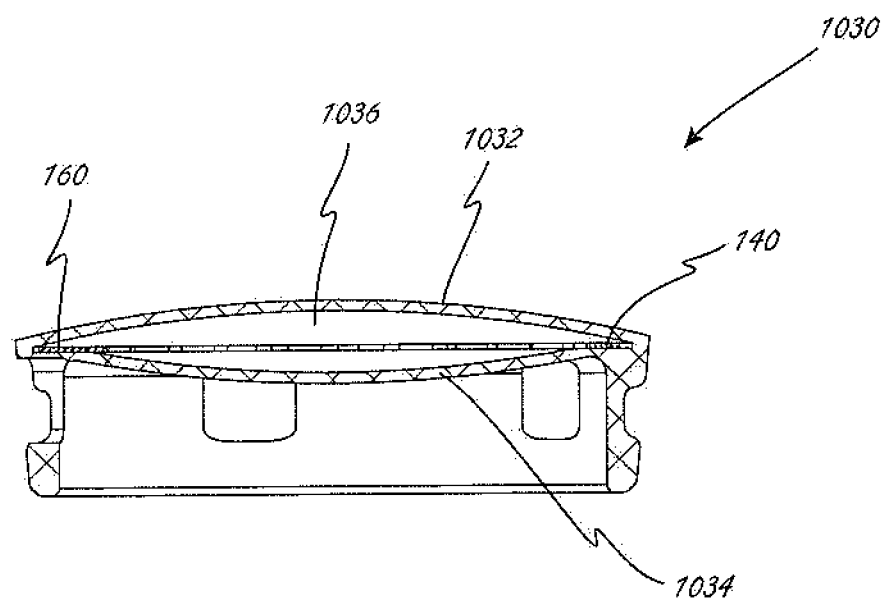
FIG. 10B is a cross-sectional view taken along section B-B of FIG. 10A.

FIG. 10A is a bottom isometric view of a fixed lens 1030, and FIG. 10B is a cross-sectional view taken along section B-B of FIG. 10A. The fixed lens 1030 is similar to the fixed lens 930 used in the modular accommodating APIOL 900 described above in FIGS. 9A-9C. The fixed lens 1030, however, includes the first and second volume control elements 140 and 160 either in lieu of or in addition to having the volume control elements 140 and/or 160 in the container. The fixed lens 1030 is itself an adjustable power lens. For example, referring to FIG. 10B, the fixed lens 1030 includes an anterior optical element 1032, a posterior optical element 1034, and a fluid chamber 1036 filled with an optical fluid and a transport substance. In operation, the first and/or second volume control elements 140 and/or 160 are exposed to a non-invasive activation energy to either decrease or increase the volume of matter in the fluid chamber 1036 and thereby adjust the optical power of the fixed lens 1030 as described above with respect to FIGS. 1-8B.

One embodiment of an oil suitable for the optical fluid 128 described above may be compounded by combining volumes of the following materials. Both equilibrium water content and refractive index can be adjusted by varying the proportions of the following components:

Phenylmethylcyclosiloxane. RI 1.545
N-(triethoxysilylpropyl)-O-Polyethylene oxide urethane, RI 1.45
(HYDROXYETHYLENEOXYPROPYLMETHYLSI-
    LOXANE)-(3,4-DIMETHOXYPHENYLPROPYL)

METHYLSILOXANE-DIMETHYLSILOXANE TERPOLYMER, RU 1.505

We claim:

1. An adjustable power intraocular lens, comprising:
   a container having an optical component and a peripheral component extending around at least a portion of the optical component, wherein the optical component has an anterior optical element, a posterior optical element, and a fluid chamber having a chamber volume between the anterior optical element and the posterior optical element;
   an optical fluid in the container;
   a transport substance in solution with the optical fluid, wherein the transport substance is configured to pass through the container; and
   volume control elements suspended in the optical fluid in the container, wherein the volume control elements are configured to be activated by a non-invasive energy and upon activation release the transport substance into the optical fluid to decrease the chamber volume and/or absorb the transport substance from the optical fluid to increase the chamber volume.

2. The adjustable power intraocular lens of claim 1, wherein the volume control elements comprise only first volume control elements configured to release the transport substance into the optical fluid to decrease the chamber volume.

3. The adjustable power intraocular lens of claim 1, wherein the volume control elements comprise only second volume control elements configured to absorb the transport substance from the optical fluid to increase the chamber volume.

4. The adjustable power intraocular lens of claim 1, wherein the volume control elements comprise:
   first volume control elements configured to release the transport substance into the optical fluid to decrease the chamber volume; and
   second volume control elements configured to absorb the transport substance from the optical fluid to increase the chamber volume.

5. The adjustable power intraocular lens of claim 4, wherein:
   the first volume control elements are activated by a first type of energy; and
   the second volume control elements are active by a second type of energy different than the first type of energy.

6. The adjustable power intraocular lens of claim 5, wherein:
   the first type of energy is selected from the group including laser energy, ultrasonic energy, electrical energy and infrared energy; and
   the second type of energy is a different type of energy selected from the group including laser energy, ultrasonic energy, electrical energy and infrared energy.

7. The adjustable power intraocular lens of claim 4 wherein:
   the first volume control elements are activated by an energy at a first wavelength or frequency; and
   the second volume control elements are activated by the same type of energy at a second wavelength or frequency different than the first wavelength or frequency.

8. The adjustable power intraocular lens of claim 7 wherein the energy is laser energy, the first wavelength is in a first bandwidth, and the second wavelength is in a second bandwidth outside of the first bandwidth.

9. The adjustable power intraocular lens of claim 7 wherein the energy is ultrasonic energy, the first frequency is in a first frequency range, and the second frequency is in a second frequency range different that the first frequency range.

10. The adjustable power intraocular lens of claim 7 wherein the energy is radiofrequency energy, the first frequency is in a first frequency range, and the second frequency is in a second frequency range different that the first frequency range.

11. The adjustable power intraocular lens of claim 1 wherein the optical fluid comprises an oil and the transport substance comprises water.

12. The adjustable power intraocular lens of claim 1 wherein:
    the peripheral component comprises an outer fluid reservoir;
    the optical component comprises an accommodating optical component in fluid communication with the peripheral component, and wherein the optical fluid flows between the peripheral component and the optical component in response to movement of ciliary muscles of a native eye;
    the volume control elements comprise (a) first volume control elements configured to release the transport substance upon activation and (b) second volume control elements configured to absorb the transport substance upon activation.

13. The adjustable power intraocular lens of claim 12 wherein:
    the optical fluid comprises an oil;
    the transport substance comprises water;
    the first volume control elements are disrupted upon activation and release the transport substance into the optical fluid, and at least a portion of the released transport substance passes out of the container thereby decreasing a volume of matter in the fluid chamber; and
    the second volume control elements are disrupted upon activation and enlarge by absorbing the transport substance from the optical fluid, and additional transport fluid from outside the container passes into the container thereby increasing the volume of matter in the fluid chamber.

14. The adjustable power intraocular lens of claim 1 wherein the volume control elements comprise:
    first volume control elements having a shell and water contained within the shell; and
    second volume control elements having a shell and a dehydrated hydrogel within the shell.

15. The adjustable power intraocular lens of claim 14 wherein the shell comprises a wax or a liposome.

* * * * *